United States Patent
Rasheed

(10) Patent No.: US 8,235,144 B2
(45) Date of Patent: Aug. 7, 2012

(54) EXPANSION AND SENSING TOOL

(75) Inventor: Wajid Rasheed, Slough (GB)

(73) Assignee: Wajid Rasheed, Slough (GB)

( * ) Notice: Subject to any disclaimer, the term of this patent is extended or adjusted under 35 U.S.C. 154(b) by 0 days.

(21) Appl. No.: 13/161,806

(22) Filed: Jun. 16, 2011

(65) Prior Publication Data

US 2011/0247878 A1     Oct. 13, 2011

Related U.S. Application Data

(63) Continuation-in-part of application No. 12/996,195, filed on Dec. 13, 2010, which is a continuation-in-part of application No. PCT/ES2009/070261, filed on Jun. 27, 2009.

(30) Foreign Application Priority Data

Jun. 27, 2008   (GB) .................................. 0811815.0

(51) Int. Cl.
 *E21B 7/30*    (2006.01)
 *E21B 44/00*   (2006.01)
(52) U.S. Cl. .............. 175/57; 175/24; 175/40; 175/263; 73/152.03; 73/152.46
(58) Field of Classification Search ............... 175/5, 24, 175/40, 57, 263; 73/152.03, 152.46
See application file for complete search history.

(56) References Cited

U.S. PATENT DOCUMENTS

| | | | | |
|---|---|---|---|---|
| 4,241,796 A * | 12/1980 | Green et al. | .................... | 175/24 |
| 5,293,945 A * | 3/1994 | Rosenhauch et al. | ...... | 175/325.2 |
| 6,918,454 B2 * | 7/2005 | Prior et al. | ....................... | 175/26 |
| 7,389,828 B2 * | 6/2008 | Ritter et al. | ....................... | 175/40 |
| 7,422,076 B2 * | 9/2008 | Koederitz et al. | ................ | 175/26 |
| 7,591,314 B2 * | 9/2009 | Sonnier et al. | ................. | 166/301 |
| 7,699,120 B2 * | 4/2010 | Desai | .............................. | 175/38 |
| 2002/0096362 A1 * | 7/2002 | Rankin et al. | .................... | 175/26 |
| 2004/0134687 A1 * | 7/2004 | Radford et al. | .................. | 175/57 |
| 2004/0222022 A1 * | 11/2004 | Nevlud et al. | .................... | 175/57 |
| 2004/0226748 A1 * | 11/2004 | Prior et al. | ....................... | 175/27 |
| 2006/0207797 A1 * | 9/2006 | Dewey et al. | .................... | 175/57 |
| 2007/0005316 A1 | 1/2007 | Paez | | |
| 2007/0056772 A1 * | 3/2007 | Koederitz et al. | ................ | 175/53 |
| 2009/0266544 A1 * | 10/2009 | Redlinger et al. | ............ | 166/298 |
| 2010/0006338 A1 * | 1/2010 | Desai | .............................. | 175/27 |
| 2010/0006339 A1 * | 1/2010 | Desai | .............................. | 175/57 |
| 2010/0089583 A1 * | 4/2010 | Xu et al. | ........................ | 166/298 |
| 2010/0224414 A1 * | 9/2010 | Radford et al. | .................. | 175/57 |

(Continued)

FOREIGN PATENT DOCUMENTS

GB     2460096 A   * 11/2009

(Continued)

*Primary Examiner* — Jennifer H Gay
(74) *Attorney, Agent, or Firm* — Loren G. Helmreich; Streets & Steele

(57) ABSTRACT

An expansion and sensing tool (50) comprising a tool body, cutter blocks and sensors which permit simultaneous underreaming and measurement of the diameter of a wellbore (40) drilled by an oil and gas rig (10). Radially extendable cutter blocks (62) incorporating positional sensors (80) contained on the block or within the body measure the position of the cutter block relative to the tool, and a vibration sensor (76) measures vibration and underreaming wellbore dimensions in real-time. Receivers, sensors and microprocessors deliver a desired wellbore depth both simultaneously comparing and correlating measured vibration data and optimizing underreaming parameters. The tool may be optionally configured with a caliper or a stabilizer.

21 Claims, 4 Drawing Sheets

U.S. PATENT DOCUMENTS

| | | | |
|---|---|---|---|
| 2010/0282511 A1* | 11/2010 | Maranuk et al. | 175/40 |
| 2011/0226531 A1* | 9/2011 | Jones | 175/50 |
| 2011/0247878 A1* | 10/2011 | Rasheed | 175/50 |
| 2011/0278064 A1* | 11/2011 | Rasheed | 175/24 |

FOREIGN PATENT DOCUMENTS

| | | | |
|---|---|---|---|
| GB | 2465504 A | * | 5/2010 |
| GB | 2465505 A | * | 5/2010 |
| WO | WO 2009156552 A1 | * | 12/2009 |

* cited by examiner

EXPANSION AND SENSING TOOL

CROSS-REFERENCE TO RELATED APPLICATIONS

This application is a continuation-in-part of U.S. application Ser. No. 12/996,195, filed on Dec. 13, 2010, which is a continuation-in-part of PCT/ES2009/070261 filed Jun. 27, 2009 which claims benefit from GB Application No. 0811815.0, filed Jun. 27, 2008, now GB Patent No. 2460096 granted Nov. 18, 2009.
Applicant Rasheed, Wajid
U.S. application Ser. No. 12/966,195
Country USA
Priority WO 2009/PCT 156552 A1 and GB0811815.0 (27 Jun. 2008) granted GB2465504

FIELD OF THE INVENTION

This invention relates to an integrated expansion and sensing tool that is capable of enlarging and measuring borehole and tubular diameters, especially wellbores in the oil and gas industry. The tool finds particular use as an underreamer capable of sensing vibration, but can also be configured with other sensors such as callipers to measure wellbore diameter.

When constructing an exploration or production well, numerous downhole operations are conducted to drill and measure a borehole so that it meets the desired well-plan. Drilling itself may utilise a reamer to ensure that the hole diameter that has been drilled by the bit is maintained within the given tolerance. The hole diameters drilled by the bit and perfected by the reamer are substantially the same as the maximum cutting diameter of a reamer, which is fixed and is substantially the same as the bit diameter. This maximum cutting diameter is defined by the pass-through diameter of any restriction in the borehole above the operating location.

In contrast to a reamer, an underreamer is used to enlarge a borehole beyond its original drilled size. Enlargement is typically done below a restriction in the borehole, and the cutting diameter of an underreamer is always greater than that of the pass-through diameter of the restriction. Additionally, an underreamer is provided with activation and deactivation modes and mechanisms for extending and retracting cutting elements to ensure effective underreaming once it has passed below the restriction.

Measurement may involve the acquisition and communication to surface of various types of wellbore data such as drilling dynamics, resistivity, porosity, permeability, azimuth, inclination and borehole diameter or rugosity, formation dips or bedding angles.

Measurement itself occurs in two modes, either wireline or logging-while-drilling. Wireline is by far the most common measurement technique and is performed as a separate and consecutive activity to drilling involving the conveyance of measurement tools on a wire or cable. Wireline calipers use a plurality of fingers to take borehole diameter measurements. However, wireline calipers can only take measurements in an axial direction. Due to this limitation, they can only be used after drilling otherwise the rotational and impact forces of drilling would cause them to break. Hence a separate caliper run is required after drilling to measure borehole diameter.

Logging-while-drilling or measurement-while-drilling tools may acquire various data from the wellbore. For drilling dynamics, measurement-while-drilling are the preferred means of acquiring drilling data such as vibration. Acoustic calipers may be incorporated within logging tools. As they can be rotated, acoustic calipers may be used while drilling to acquire measurement data. However, almost all logging tools are configured as complete systems and are only available at very high cost. Further they also suffer from limitations in applications with slide drilling, where a downhole motor rotates the bit and drags the drillstring and bottom-hole assembly, or BHA. Or in Rotary steerable applications where they are configured near to the bit. Therefore, the location of the sensor is within the BHA below the underreamer. It can only give readings after the section has been underreamed.

Presently, borehole measurements do not provide for drilling dynamics data specifically acting on the underreamer. It is routine for drilling dynamics data to be taken below the underreamer but this does not in any way characterize the forces acting on the underreamer.

Further, wellbore diameter measurements are often not taken and the time-lag associated with the separated operations of enlargement and measurement leads to uncertainty and unnecessary cost. In the case of underreaming, wellbore measurements are taken after underreaming, which means a separate caliper run and at times further corrective runs to attain the desired wellbore diameter.

Further, as drilling has already been completed and no vibration data was acquired directly above the underreamer, there are no means of measuring the actual forces acting on the underreamer or its behaviour in real-time. The present invention is differentiated in this aspect as it provides real-time drilling dynamics data of the underreaming operation which would enable a driller to identify a vibration mode and change drilling conditions to eliminate the vibration. This would reduce harmful vibrations which are a major cause of downhole tool failures as well as the lower rates of penetration related to underreaming in medium to hard formations or interbedded formations.

BACKGROUND OF THE INVENTION

Oil and gas accumulations are found at depth in different geological basins worldwide. Exploration and production of such accumulations rely on the construction of a well according to a well plan.

Various well types exist and are defined according to usage such as wildcats or those used in exploration; delineation; and production and injection. Variations in well profile exist also according to vertical, slant, directional and horizontal trajectories. Each differs according to the oil company's objectives and the challenges that a given basin presents from the surface of the earth or the ocean to the hydrocarbon reservoir at a given underground depth.

Engineering challenges are related to the location of the well-site such as onshore or offshore, seawater depths, formation pressures and temperature gradients, formation stresses and movements and reservoir types such as carbonate or sandstone. To overcome these challenges, a highly detailed well plan is developed which contains the well objective, coordinates, legal, geological, technical, well engineering and drilling data and calculations.

The data is used to plot a well profile using precise bearings which is designed in consecutive telescopic sections-surface, intermediate and reservoir. To deliver the well objective and maintain the integrity of well over its lifecycle, a given wellbore with multiple sections and diameters is drilled from surface. Although there are many variants, a simple vertical well design could include a surface or top-hole diameter of 17½" (445 mm), intermediate sections of 13⅝" (360 mm) and 9⅝" (245 mm) narrowing down to the bottom-hole diameter of 8½" (216 mm) in the reservoir section.

Each consecutive section is 'cased' with the specified diameter and a number of metal tubes placed into the wellbore according to the length of the section. Each must be connected to each other after which they are cemented into the appropriately sized hole with a given tolerance. In this way, a well is constructed in staged sections, each section dependent on the completion of the previous section until the well is isolated from the formation along the entire distance from surface to the reservoir.

Scarcity of oil and gas is driving oil and gas companies to explore and develop reserves in more challenging basins such as those in water-depths exceeding 6,000 ft (1830 m) or below massive salt sections. These wells have highly complex directional trajectories with casing designs including 6 or more well sections. Known in the art as 'designer' or 'close tolerance casing' wells, these wells have narrow casing diameters with tight tolerances and have created a need to enlarge the wellbore to avoid very narrow diameter reservoir sections and lower production rates.

Therefore, the bottom-hole assemblies that are needed to drill these wells routinely include devices to underream the well-bore below a given casing diameter or other restriction. In this way, underreamed hole size has become an integral part of well construction and there is now an increased dependence on underreaming to meet planned wellbore diameters.

To those skilled in the art, it is known that underreaming activities generate uncertainty as to drilling dynamics and enlarged wellbore diameter. This is because the prior art does not provide for drilling dynamics data acting on the underreamer. If any drilling data is provided, it is in the pilot hole or where drilling has already taken place. Consequently, the lack of underreaming dynamics and vibration data results in a limited understanding of the actual loads and forces acting on the underreamer in real-time.

The present invention is differentiated in this aspect as it provides real-time drilling dynamics data of the underreaming operation which would enable a driller to identify a vibration mode and change drilling conditions to eliminate the vibration. This would reduce harmful vibrations which are a major cause of downhole tool failures as well as the lower rates of penetration related to underreaming in medium to hard formations or interbedded formations.

The data maybe transmitted in real-time by means of data transfer (mud pulse telemetry, fibre-optic or other) or maybe stored in memory and downloaded at a later time. The present invention would make underreamed drilling data available and optimize underreaming operations thereby reducing failures and improving drilling efficiency.

The present invention provides for a novel approach that measures underreaming drilling dynamics and pilot hole drilling dynamics considering the two as separate but inter-related with each subject to different levels of vibration, weight, torque, bending moments, accelerations etc. Typically, an underreaming run has no means of investigating drilling dynamics at the underreamer and therefore corrective actions are limited to reducing the rate of penetration, reducing the rotary speed, reducing the weight on bit.

Drilling vibration occurs in two modes which are classed as resonant i.e. torsional, axial, lateral and non-resonant vibration, i.e. eccentric, sudden modes releasing stored torque known as backward rotation and whirl. Each mode maybe defined separately but in reality all modes are experienced during drilling, the severity of each level depends on the drilling BHA design, drilling dynamics and geological formations. Axial vibrations are often manifested as a stick-slip condition where weight applied at surface causes compression of the drill-string. Due to the geometry of the wellbore and bending moments, the weight is concentrated at the widest diameters of the drill-string which is the underreamer, stabilizers, rotary steerables and the drill-bit.

By detailing the exact nature of vibration at the underreamer, the present invention would be able to alert the driller when vibration reaches a certain level, therefore highlighting a change in drilling parameters or geological conditions that have caused such a change. Previously, this would not be possible and drilling delays could occur.

Previously, to overcome the lack of underreaming drilling data the industry has relied on models of the bit and underreamer wear in varying formations to investigate the effects that formation loading has on both. However, the models are based on predicted values rather than actual measurements. In this way, the present invention would not only optimise drilling during underreaming operations but also provide for accurate input data for modelling drilling dynamics.

The present invention would characterize underreamer dynamics during drilling and would highlight wear and avoid premature failures due to tool design weak spots or usage related to surface or downhole parameters as well as to optimise the rate of penetration and hole cleaning.

In the aspects of a sensing underreamer tool capable of measuring drilling dynamics and eliminating downtime and premature failures, the present invention is differentiated from the prior art underreamers. These are unsatisfactory as they there are no actual underreaming drilling dynamics measurements whether direct or inferred.

It is unsatisfactory to depend on indirect indicators such as whether cutter blocks are open or closed or whether fluid pathways are open and a pressure spike is seen at the rig floor to indicate activation. Such indicators do not provide actual measurements of the underreamed well-bore underreamed nor do they provide verification of underreaming performance; they simply give information on the mechanical or hydraulic status of an aspect of the tool which may or may not lead to the desired well diameter.

To those skilled in the art, it is known that the industry relies on even more rudimentary and time-consuming indicators of verification such as an increase in drilling torque as cutters interact with the formation or even pulling up the drill-string and underreamer to the previous hole size in order to see whether the top-drive stalls as the bottom-hole assembly gets stuck due to the expanded tool. Or by drilling a pilot hole section with the underreamer deactivated and pulling back into the pilot hole.

In the specific aspect of drilling dynamics and underreaming behaviour, the ability to acquire accurate data on vibration, stick-slip, loads and other accelerations by means of the present invention optimally differentiates it from prior art. Prior art underreamers do not provide for in-situ data measurements on drilling dynamics or loads and therefore their performance, design or configuration cannot be optimized from one job to another.

A major drawback of prior art underreamers is their cutting performance in terms of maintaining similar rates of penetration to the bit. To one skilled in the art, it is known that the bit has optimized designs due to the well characterized drilling dynamics which is well understood by means of measurement-while-drilling data acquired in the pilot-hole. Further cutter element placements and nozzle locations are optimized in the drill-bit and not necessarily so in the underreamer and this often leads to the bit outperforming the underreamer.

Consequently, this leads to either a separate underreaming run after drilling the section, or leads to the underreaming-while-drilling itself taking several attempts before a complete section is underreamed satisfactorily. In terms of drilling dynamics, the optimised drill-bit drills at a faster rate of penetration than the underreamer which has trouble maintaining similar rates of penetration. Due to the distances between the bit and underreamer which maybe 120' or more, the bit may have exited a hard formation or layer while the underreamer may just be entering the earlier hard formation or hard layer as it is may not be connected directly to the bit. The prior art underreamers do not provide for measurements of the drilling dynamics concentrated at the underreamer.

Therefore, the prior art does not lend itself to a reliable or certain means of measuring underreaming drilling dynamics in real-time or memory mode.

Further the prior art perpetuates drilling inefficiencies due to the uncertainty of actual vibrations at the underreamer.

Further the prior art does not provide for accurate input into underreaming and drilling models.

Further the prior art does not allow for the timely identification of vibration modes or their correction in real-time.

SUMMARY OF THE INVENTION

The present invention has for a principal object to provide an improvement on the prior art wherein the actual drilling loads and vibration experiences in the underreamed hole is measured directly in real time, that is to say simultaneously with, or immediately after, an expansion operation.

The invention seeks to meet the need for an integrated underreamer and drilling dynamics sensor, which provides for real time drilling dynamics performance verification and automated troubleshooting in the underreamed hole. This has not been forthcoming in the prior art.

The present invention seeks to provide accurate input into underreaming and drilling models by using real-time or memory mode data based on in-situ vibration levels rather than the predicted values.

The present invention optimizes drilling efficiency by identifying the optimal operational parameters to ensure minimized vibration thereby increasing tool life and minimizing the need for corrective underreaming runs by providing real-time drilling dynamics data which allows the driller to respond earlier thereby saving time and money.

It is thus an object of the present invention to provide sensors integrated within an underreamer, enabling the integrated device to give immediate measurement of the vibration levels sustained during the wellbore-widening operation and, if these are found to be critically high, to automatically reconfigure drilling parameters to bring vibration levels to satisfactory levels in real-time or to perform such analysis in memory mode and provide input for drilling dynamics models.

Although underreaming is a principal route to wellbore enlargement, the invention envisages alternative enlargement means similarly integrated with sensor measurements of the enlarged bore. These alternative means could include bicentre bits, fixed wing bits, eccentric underreamers and expandable bits.

It is a further object to provide a tool capable of simultaneously conducting well-bore enlargement, measuring vibration or stick/slip levels within the enlarged wellbore, taking calliper measurements preferably by an acoustic echo-pulser and sensor, and verifying performance through a processor arrangement that uses sensor data to detect undergauge hole and conducts diagnostics according to a logic circuit in order to ensure the underreamer is functioning correctly. If the corrective steps have been taken and the calliper indicates that the planned hole diameter is still not being delivered a signal may be sent to the rig-surface or to the location of the operating engineer so that further remedial action can be taken, such as tool replacement. A memory mode may store sensor information that can be downloaded at surface when the tool is retrieved, or sent to the surface by telemetry.

The tool may also have a built-in link to a mud-pulse telemetry system to allow real-time monitoring of the underreaming operation. One or more sensors may be optimally spaced in order to detect a number of conditions during a given time period within the enlarged wellbore.

A keyway may provide a channel for wiring from the sensors to the processor and transponder. The wiring can be used to transmit data retrieved by the vibration sensors, as well as positional data from the mechanical blocks, to the processor and transponder. The keyway may be sealed and filled with a means to absorb vibration such as silicon gel or grease and to maintain wires in position.

The transponder converts data so that it can be transmitted and is linked to the mud-pulser which transmits the data to surface using a series of binary codes at a given frequency using drilling fluid as means of mud pulsing. Other means of data transfer may be used such as wireless transmission short hop using radio frequency or electro-magnetic pulses or fibre-optics. This allows up and downlink of the tool in order to receive and transmit data and commands.

At surface a transducer may be incorporated within a decoder housing which decodes the binary code and may link to the driller's terminal or may be yet further transmitted by satellite or other means to a remote operations centre.

These and other objects will emerge from the following description and the appended claims.

In one aspect, the invention provides an expansion and sensing tool comprising a tool body, means for attaching the tool body directly or indirectly to a support whereby it can be rotated and moved axially along a borehole below a restriction, at least one expansion element adapted to be extendable from the tool body to an expansion diameter greater than the restriction, and sensing means housed within the tool body and adapted to measure drilling dynamics as expanded by the expansion element during or immediately after expansion. The support may typically be a drill string or an extended length of coiled tubing, as used in downhole operations in oil and gas fields.

In preferred embodiments of the invention, the expansion operation is an underreaming application, and expansion elements comprise a set of cutter blocks optimally configured with cutter inserts and nozzles. Alternatively, the expansion elements may comprise expansion blocks, which may be of similar construction to the cutter blocks, but having outer surfaces where cutter elements may be replaced by a hardened material. Such expansion blocks may simply bear under pressure against the inside of a tubular wall, with sufficient force to deform it outwardly to a larger diameter. In yet another alternate configuration, the same blocks may simply bear against the underreamed wellbore in order to stabilize the tool within the wellbore without enlarging the bore. The same blocks maybe received within an additional section of the tool or a separate steel body suitably prepared to provide a means of stabilization to the expansion operation. Alternatively, the same blocks maybe received within an additional section of the tool or a separate steel body suitably prepared to provide a means of stabilization for underreaming applications.

It is to be noted that the description herein of the structure and operation of cutter or expansion blocks is applicable generally, irrespective of function, except to the extent that cutter inserts may be provided specifically for underreaming purposes and removed for expansion purposes.

The tool body is typically a cylindrical high grade steel housing adapted to form part of a bottom-hole assembly (BHA). Thus the means for attaching the tool body to the support, whether it is a drill string or coiled tubing, may comprise a screw thread provided on the tool body which is engageable with a drill collar. The attachment to the drill string need not be direct, but may be indirect, as there will typically be many different functional elements to be included in the long and narrow BHA, and the arrangement of the successive elements may vary. The lower end of the BHA may be the drill bit, or a bull nose, and in between there may or may not be a means for directional control such as a rotary steerable system. The tool body may be provided with a through passage for the flow of drilling fluid from the drill string.

The set of cutters may comprise a cutter block carrying a plurality of cutter elements directed outwardly of the tool body. The cutter block may be received within the tool body in a cutter block chamber having an open mouth, and the cutter may be extendable from the chamber through the chamber mouth with the cutter elements projecting from the tool body, and retractable back into the chamber. The cutter elements may be polydiamondcrystalline inserts, or other inserts according to requirements.

The tool may then be provided with means for extending and retracting the cutter block from and into the cutter block chamber. The microprocessor control means may be suitably adapted to receive drilling dynamics data from the sensor means and to control the drilling operation or the position of the block in response thereto.

The tool may comprise means for monitoring the extension and retraction positions of the cutter block in the cutter block chamber. The tool normally comprises a plurality of such cutter blocks, arranged symmetrically around the tool. Two cutter blocks would be on opposite sides of the tool, three blocks would be separated by 120 degrees, four by ninety degrees, and six by sixty degrees. In operation, the underreaming tool is typically rotated on the drill string as well as being moved axially along the wellbore.

In accordance with a particularly preferred aspect of the invention, the cutter block is provided with an internal duct for directing drilling fluid from a source to an external nozzle among the cutter elements. The source of drilling fluid may be the drill-string or other support for the tool, and the aforementioned through passage for the flow of drilling fluid from the drill string to the drill bit. Alternatively or additionally, the tool body may be provided with an internal duct receiving a source of drilling fluid flowing to an external nozzle adjacent the set of cutters. In each case, the nozzle provides a fluid flow that can help to keep the cutters clean and prevent the build-up of clogging debris from the reaming operation, remove such material altogether from the underreaming zone, and provide a cooling and lubricating function for the cutters.

In a preferred aspect the present invention incorporates a non-mechanical means of wellbore diameter measurement which is practically applicable and may be an acoustic calliper.

In another preferred aspect of the present invention housing for a mechanical calliper is provided within the cutter block which offers a robust location. This has not been possible with previous underreamer blocks due to their inherent design limitations which rely on the block base as a retention mechanism or hydraulic activation through drilling fluid pressure.

The calliper means may typically be housed within the tool body above the underreamer, but in a variation a mechanical caliper may be located within the cutter block optimally located among the most radially extended cutter elements or surface.

The underreaming tool may further comprise telemetry means for communicating drilling dynamics data and control signals between the tool and a surface interface, which may, among other functions, control the drill string during the underreaming operation.

In a further aspect, the invention provides a method of operating an expansion tool to enlarge a borehole or tubular or the like to a target dimension below a restriction, which comprises locating a tool according to the invention in a borehole on a support below a restriction, extending the expansion element to an expansion diameter greater than the restriction, in a preferred embodiment a set of cutters to an underreaming diameter greater than the restriction, rotating the tool and moving it axially along the borehole on the drill string or other support, measuring drilling dynamics by the vibration sensor means, measuring the bore diameter by the calliper means, and continuing the expansion operation until the target dimension is achieved.

In accordance with the method of the invention, the tool may be provided with expansion element extension control means responsive to dimension data received from the sensor means. In this way, an integrated tool which is capable of detecting vibrations and correcting it may be realised. The drilling dynamics data may prompt a surface monitor to signal an opportunity for operator intervention.

Thus, in the case of an underreaming tool with vibration sensing means, data from a sensor may be transmitted to a processor which may use this data to correlate whether vibration levels exceed acceptable levels. Where the processor detects a fault or difference, it automatically troubleshoots the fault using a logical procedure.

For example, the processor may be programmed with a logic circuit which can be configured in any number of ways so as to optimize performance. An exemplary configuration may involve the circuit to first establish vibration levels. If these exceed given limits then it can alert the user by means of mud pulse telemetry, fibre optics or other data transmission to check operational parameters such as weight or surface rotational speed. The skilled man will readily appreciate that other procedures may be implemented by the logic circuit within the processor, which can be programmed to cover other scenarios.

The expansion block means may comprise a cutter block carrying cutter elements directed outwardly of the tool body.

In a still further aspect, the invention provides an underreaming tool comprising a tool body and a cutter block carrying a plurality of cutter elements directed outwardly of the tool body, wherein the cutter block is received within the tool body in a cutter block chamber having an open mouth, and means for extending the cutter block from the chamber through the chamber mouth with the cutter elements projecting from the tool body, and for retracting the cutter block back into the chamber, wherein the cutter block is provided with an internal duct open to a source of drilling fluid to an external nozzle among the cutter elements.

Alternatively, other expansion block means may replace the cutter block with its cutter elements.

BRIEF DESCRIPTION OF THE DRAWINGS

Embodiments of the invention are illustrated by way of non-limiting examples in the accompanying drawings, in which.

DETAILED DESCRIPTION OF THE INVENTION

Figure 1:
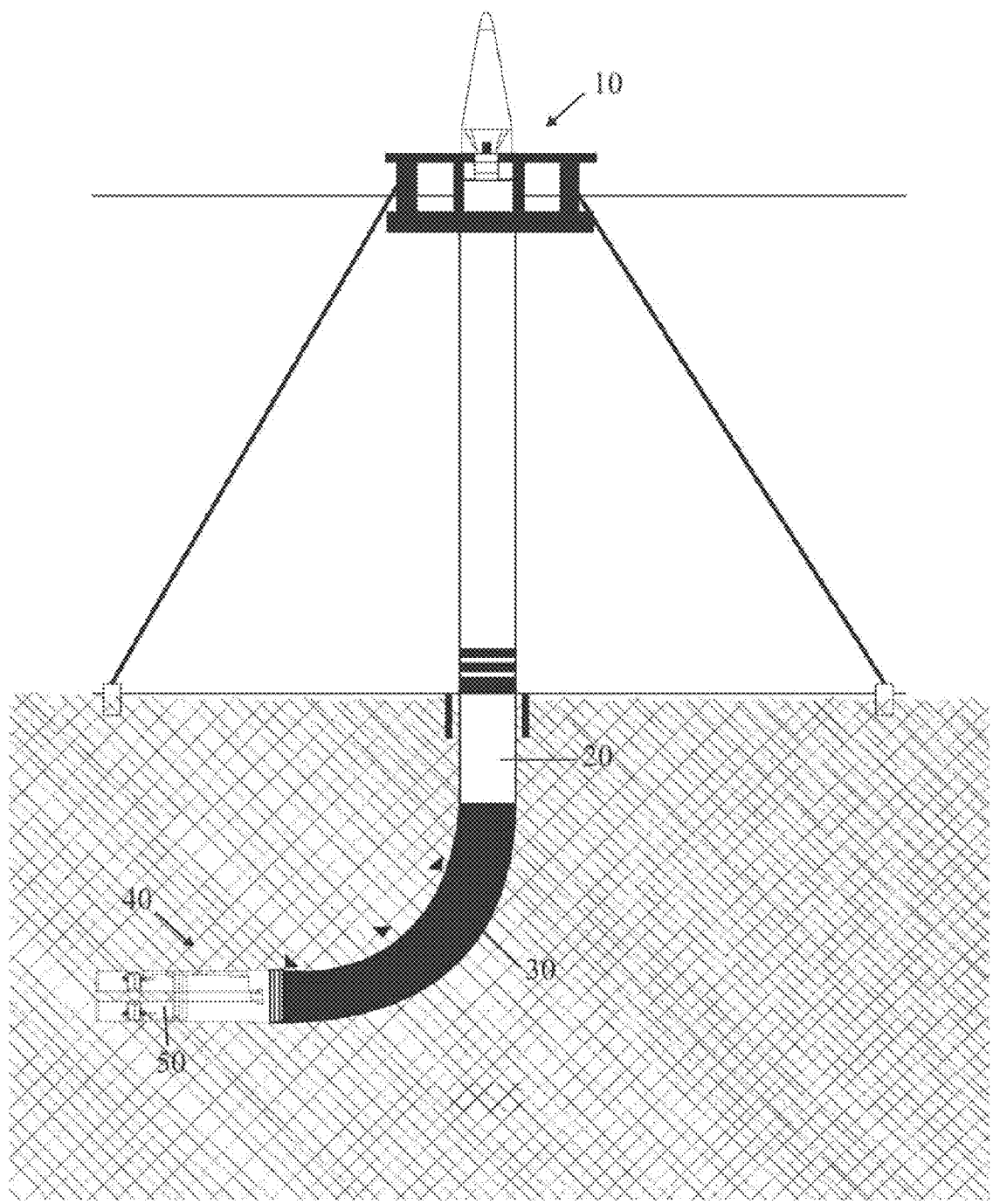
FIG. 1 is a general diagrammatic view of an oil or gas well showing surface structures and the underground wellbore, with a tool in accordance with the invention as part of a bottomhole assembly.

As shown in FIG. 1, an exemplary exploration or production rig comprises a surface structure 10 at the wellhead, a wellbore 20, and a drill string 30 in the wellbore with a bottom-hole assembly 40 at its lower end. The bottom-hole assembly includes an underreamer sensing tool 50 in accordance with the invention, and a drill-bit (not shown).

Figure 2A:
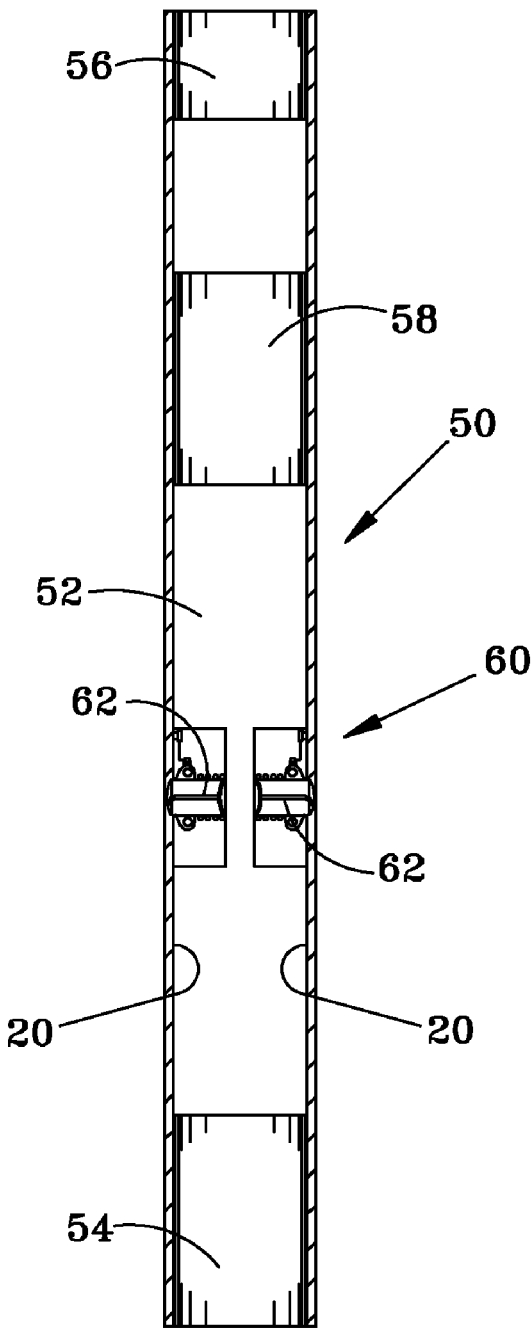
FIG. 2a is a side elevation, part cut away to show the expansion elements in a deactivated state, of the tool of FIG. 1.
Figure 2B:
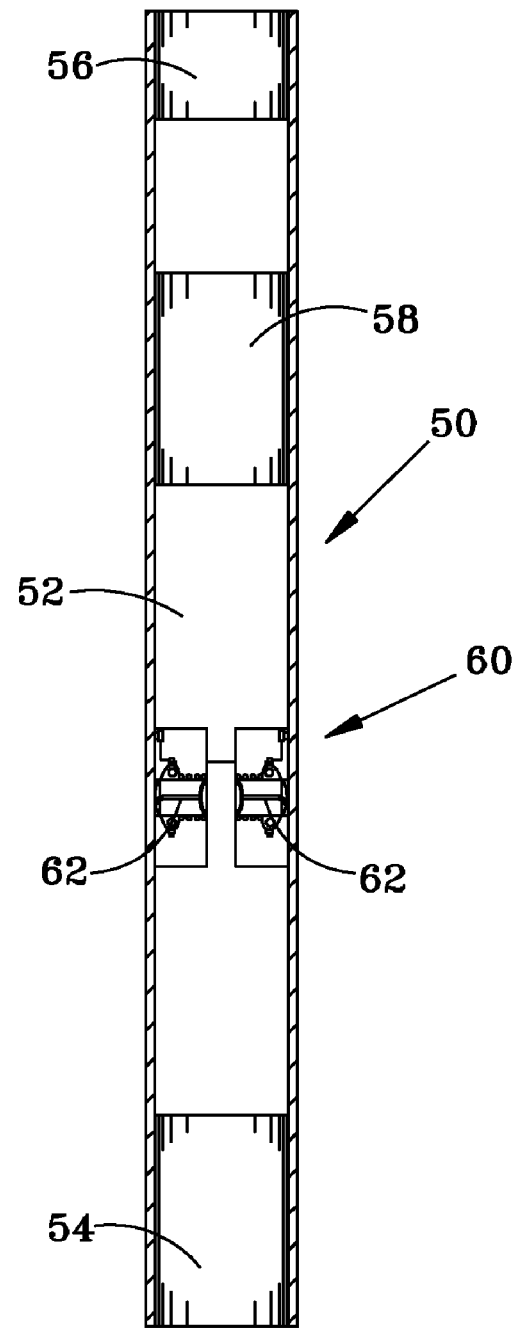
FIG. 2b is a side elevation corresponding to FIG. 2a showing the expansion elements in an activated state.

The integrated expansion and sensing tool 50 is illustrated in FIGS. 2a and 2b, and comprises a tubular steel body 52 provided with a drilling collar 54 at its downhole end and a mud-pulser 56 at its other end, which is adapted to be engaged by a further drill collar (not shown) to connect it other elements of the bottom-hole assembly 40, and then to the drill string 30.

The tool body also carries a vibration sensor 76 and an expansion element assembly 60 between the vibration sensor and the drill collar 54. The expansion element assembly 60 comprises a number of expansion blocks 62 disposed symmetrically, radially around the tool body 52, and in the deactivated condition shown in FIG. 2a the blocks are withdrawn into the tool body, but in the activated condition shown in FIG. 2b the blocks are extended beyond the tool body against the wellbore 20. An exemplary configuration may involve the circuit to first cross check the cutter block positional data from a magnetic strip 96 and sensor 94 which is placed on each cutter block and its housing. The signal that is constantly created by the magnetic strip is at strongest when the block is fully extended and the strip 96 and sensor 94 are aligned. In this way, it can be seen whether the block has actually been extended. If the block has 10 been extended yet the caliper data shows that the actual wellbore is below the planned wellbore size, then it can alert the user by means of mud pulse telemetry to check operational parameters such as drilling fluid pump rates or surface rotational speed.

Figure 3:
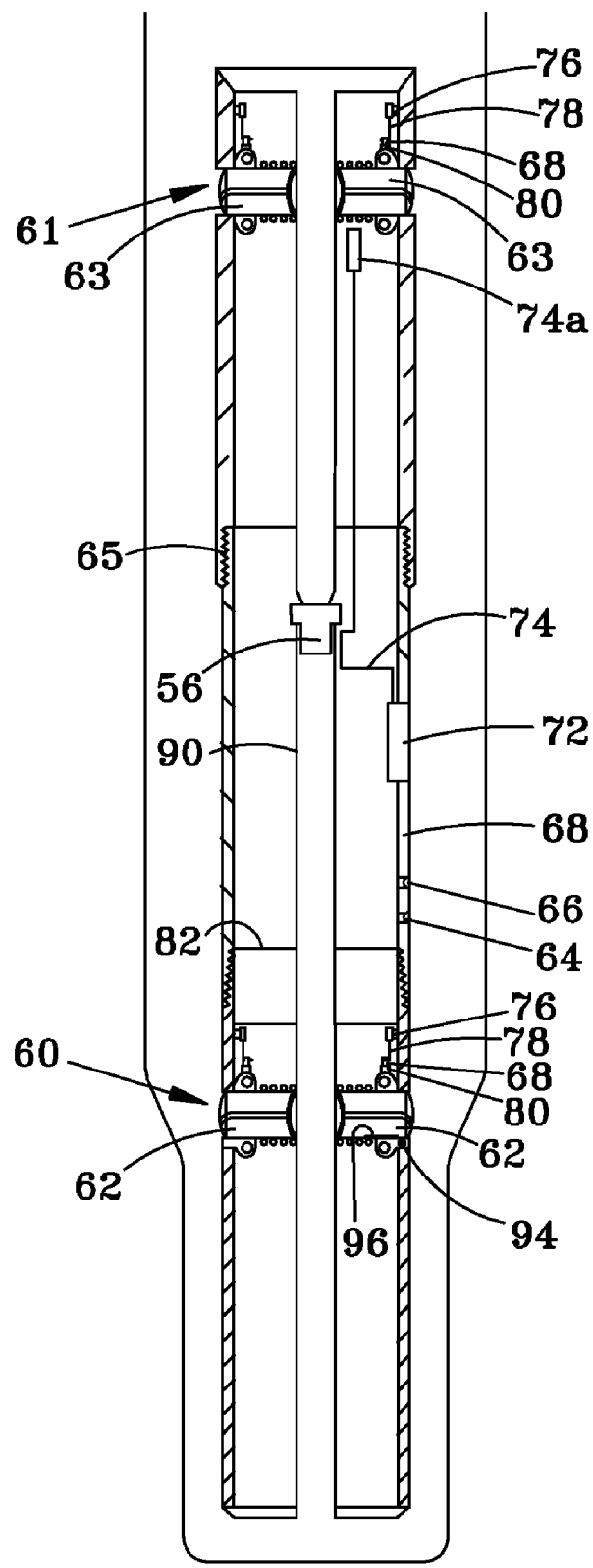
FIG. 3 is a diagrammatic cross section through an underreaming and sensing tool in accordance with the invention similar to that shown in the previous Figures, but having an additional stabiliser section at the trailing uphole end.
Figure 4:
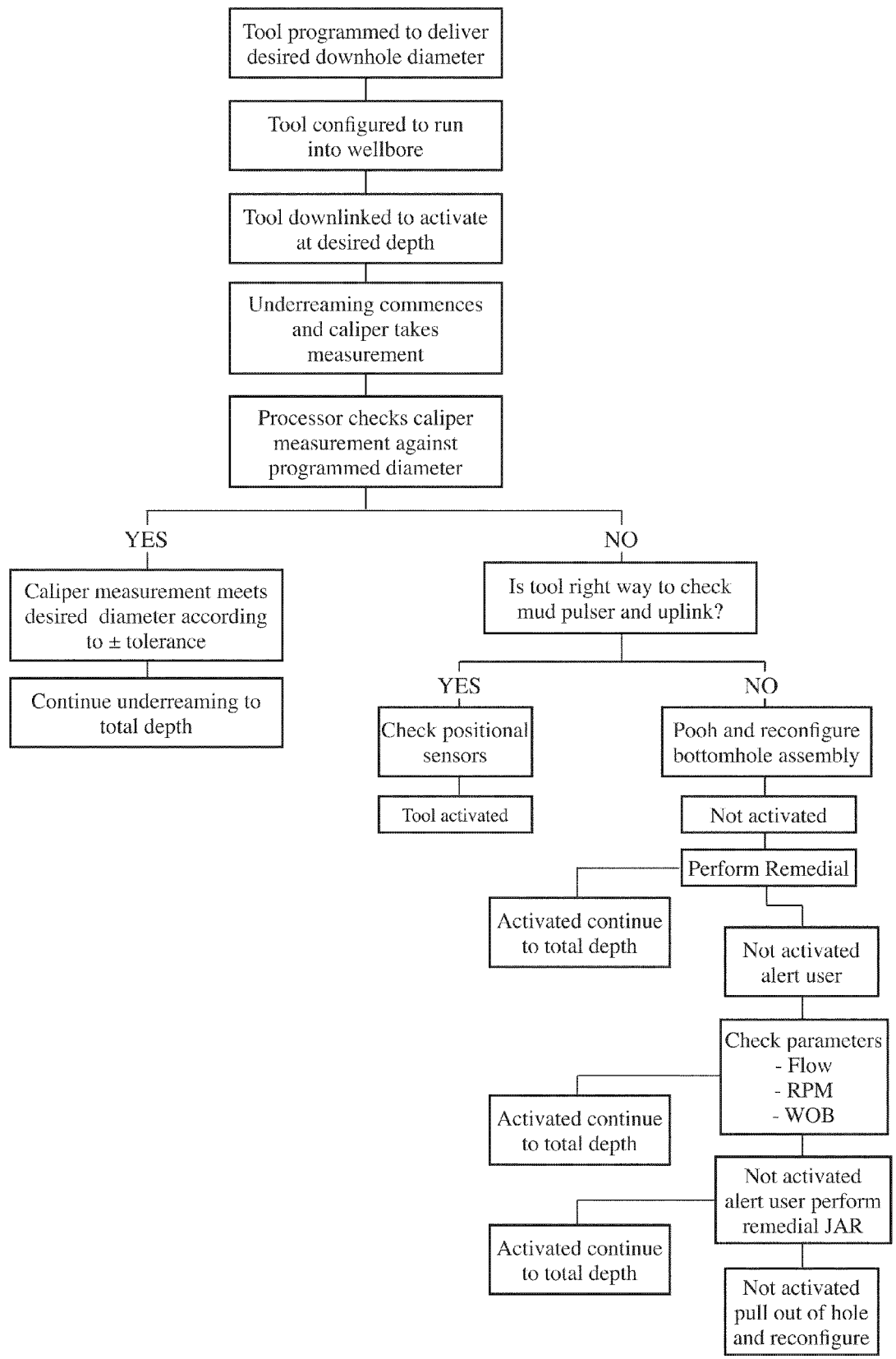

FIG. 3 illustrates diagrammatically the aforementioned elements of the tool 50, together with a stabilizer section 61.

As the sensor means 76 indicated in FIG. 3, further sensors may be incorporated in 64 or 66. Data is processed using a micro-processor 68, shown in two alternative locations, that correlates data from the sensor 66 to detect a critical condition or simply store data for further analysis. The tool is also programmed and automated to conduct diagnostics according to a logic circuit or diagnostic program stored in processor 68 in order to ensure the underreamer is functioning correctly. Once corrective steps have been taken, and if drilling dynamics are still not optimised, an alert signal is sent via the mud-pulser 56 to the rig-surface 10 or to a remote operator so that further remedial action such as the replacement of the BHA 40 can be considered. A memory module associated with processor 68 may store sensor information that can be downloaded at surface when the tool is retrieved, or sent to the surface by telemetry through mud-pulser 56.

The tool is provided with a built-in link to a data transfer system 56 which also serves to monitor real-time drilling dynamics. One or more sensors placed in 76, 64 or 66 are spaced within the tool body 52 in order to detect vibrations during drilling caused by formations in the near wellbore 20.

As further shown in FIG. 3, a keyway 74 provides a channel for wiring from the sensors 66 to the processor 68, and also to a transponder 72. The wiring is used to transmit data retrieved by the sensors to the processor and transponder. The keyway may be sealed and filled with a means to absorb vibration and maintain wires in position such as silicon gel or grease.

The transponder 72 converts data from microprocessor 68 so that it can be transmitted to surface 10 and is linked to the mud-pulser 56 which transmits the data to surface using a series of binary codes at a given frequency using drilling fluid as means of mud pulsation. Other means of data transfer may be used such as wireless transmission, short hop using radio frequency or electro-magnetic pulses.

FIG. 3 also shows an alternative location for a sensor, in housing 66 or 64 connected to wiring in keyway 74 and further wiring 78 to alternative processor location 68 FIG. 3 also shows a central axial through passage 90 for the flow of drilling fluid through the whole bottom-hole assembly 40.

The sensor means 76, 58, or 64, 66, is typically housed within the tool body 52 above the underreamer 60, but in a variation a caliper 76, 122 may be located within the tool.

The tool body 52 is a cylindrical high grade steel housing adapted to form part of a bottom-hole assembly (BHA) 40. FIG. 3 shows an internal connection 82 joining two parts of tool body 52. At the leading downhole end of the tool is a section housing the cutter blocks 62. Connection 82 joins this to a central section housing measurement and control functions. A further section 61 at the uphole end, joined by connection 65, houses stabiliser blocks 63 which are constructed and housed substantially identically to the underreamer components generally designated 60, except that in place of cutter elements on cutter blocks there is at least one surface which is hard faced or coated with a hard abrasion-resistant material. A similar construction can be used to expand a deformable bore, such as a steel tubular. The means for attaching the tool body to a drill string or coiled tubing comprises a screw thread (not shown) provided on the tool body which is engageable with a drill collar (not shown).

In this alternative configuration the tool is configured, in addition to underreaming capacity, with the underreaming tool body incorporating hard facing cutter blocks to act as a stabiliser. The hard facing acts to prevent cutter abrasion while reaming or stabilising the underreamed hole. This eliminates some of the problems associated with loss of directional control due to the undergauge stabiliser above the underreamer.

The stabiliser may be directly or indirectly connected to the underreamer and hard-wired accordingly so as to ensure the mud-pulser may transmit data to surface. The tool may be provided with a mud-pulser as a standalone tool or the mud pulser itself may be provided by a third party as would be the case when a measurement while drilling or logging while drilling suite of tools is located in the BHA below the present invention. The hard wiring configuration of the tool may be changed to suit such an application.

The tool normally comprises a plurality of such cutter blocks 62, arranged symmetrically around the tool. Two cutter blocks are on opposite sides of the tool, three blocks are separated by 120 degrees, four by ninety degrees, and six by sixty degrees. In operation, the underreaming tool 50 is typically rotated on the drill string as well as being moved axially along the wellbore.

As noted above, the invention provides a method of operating an underreaming tool to enlarge a borehole to a target dimension below a restriction, which comprises locating a tool as claimed in any one of the preceding claims in a borehole on a drill string below a restriction, extending the set of cutters to an underreaming diameter greater than the restriction, rotating the tool and moving it axially along the borehole on the drill string, measuring drilling dynamics by the sensor means, and continuing the underreaming operation until the target depth is achieved.

In addition to the above, the tool may be provided with a caliper means and cutter extension control means responsive to dimension data received from the calliper means.

Those skilled in the art will appreciate that the examples of the invention given by the specific illustrated and described embodiments show a novel underreaming tool and system and method for underreaming, with numerous variations being possible. These embodiments are not intended to be limiting with respect to the scope of the invention. Substitutions, alterations and modifications not limited to the variations suggested herein may be made to the disclosed embodiments while remaining within the ambit of the invention.

What is claimed is:

1. A tool comprising a tool body, at least one radially extendable cutter block, each of the at least one cutter block radially movable from a retracted position substantially within the tool body to an extended position radially outward of the tool body, the tool attached to and rotatable by a drilling support to underream, and a position sensor comprising a strip and a sensor to measure a position of the at least one cutter block relative to the tool body, the tool further comprising:
the at least one radially extendable cutter block supporting one of the strip and the sensor, and the tool body supporting the other of the strip and the sensor to measure the position of the at least one cutter block relative to the tool body, a vibration sensor to measure vibration of the tool, and the position sensor and the vibration sensor being in communication with a microprocessor to optimize drilling dynamics by comparing position sensor data and vibration signal data.

2. The tool of claim 1, wherein said microprocessor compares position sensor data to other data and stores position sensor data in memory.

3. The tool of claim 1, wherein the vibration sensor measures stick/slip data and the microprocessor optimizes drilling dynamics by comparing stick/slip data with other data.

4. The tool of claim 3, wherein said microprocessor stores stick/slip data in memory.

5. The tool of claim 3, further comprising:
a telemetry system for communicating said sensor data and other control signals between the tool and a surface interface in real-time so as to optimize drilling performance.

6. The tool of claim 1, further comprising:
the microprocessor receiving vibration data from the vibration sensor to detect vibration in real-time.

7. The tool of claim 1, further comprising:
a telemetry system for communicating sensor data between the tool and a surface interface in real-time to optimize drilling performance.

8. An apparatus, comprising:
at least one expansion elements housed in a first tool body, the at least one expansion element radially movable from a retracted position substantially within the first tool body to an extended position radially outward from the first tool body to underream the wellbore; and
at least one expandable stabilizer block supported in a second tool body, the at least one stabilizer block movable from a retracted position substantially within the second tool body to an extended position radially outward from the second tool body to stabilize the apparatus in the wellbore;
one or more sensing elements each supported on a third tool body connected to the second tool body, adapted wherein the one or more sensing elements measure drilling dynamics;
a calliper element for measuring wellbore diameter; and
data from the calliper element is compared with data from the one or more sensing elements.

9. The apparatus as claimed in claim 8, wherein the at least one expansion element is provided with cutter inserts, and the apparatus is provided with a through passage for the flow of drilling fluid which exits the tool from a nozzle adjacent the at least one expansion element.

10. The apparatus as claimed in claim 8, wherein the at least one expandable stabilizer block is provided with stabilizing surface, and apparatus is provided with a through passage for the flow of drilling fluid to the expansion elements.

11. A method of operating an expansion tool to enlarge a borehole or tubular or like passage to a target dimension beyond a restriction, comprising:
locating a tool body in a borehole on a support below a restriction;
providing at least one cutter block radially movable from a retracted position substantially within the tool body to an expanded positioning radially outward of the tool body;
extending at least one cutter block to an expansion diameter greater than the restriction;
rotating the tool while moving the tool axially along the borehole on the support;
measuring a position of the at least one cutter block;
measuring vibration with a vibration sensor;
measuring wellbore diameter with a calliper element;
data from the calliper element is compared with data from the vibration sensor and block positional.

12. The method as claimed in claim 11, further comprising:
forwarding data using at least one mud pulse to a surface interface, wherein the surface interface controls movement of the drill string.

13. The method of claim 11, further comprising:
recording the position of the at least one cutter block.

14. The method of claim 11, further comprising:
providing a rotary steerable device for directional control of the drill string.

15. A tool, comprising:
at least one expandable stabilizer block housed in a tool body, the at least one expandable stabilizer block, radially movable from a retracted position substantially within the body to an extended position radially outward from the body;
the at least one expandable stabilizer block supporting one of a strip and a position sensor, and the tool body supporting the other of the strip and the position sensor to sense a position of the at least one stabilizer block relative to the tool body;
one or more sensing elements each supported on a sensing body connected to the expandable stabilizer body, the at least one expandable stabilizer block adapted to stabilize the tool in the wellbore; and
wherein the one or more sensing elements measure drilling dynamics; and
a calliper element for measures wellbore diameter; and data from the calliper element is compared with data from a vibration sensor and block positional data.

16. A tool of claim 15, wherein:

the at least one expandable stabilizer block housed in a tool stabilizer body and radially movable from a retracted position substantially within the expansion body to an extended position radially outward from the expansion body to stabilize the tool in the wellbore;

the one or more sensing elements each supported on- a sensing body connected to the stabilizer body, and the one or more sensing elements sense drilling dynamics.

17. A tool, comprising:

at least one movable expandable stabilizer block;

each of the at least expandable stabilizer block radially movable from a retracted position substantially within the tool body to an extended position radially outward of the tool body;

the tool attached to and rotatable by a drilling support to underreaming;

a position sensor comprising a strip and a sensor, one of the strip and the sensor supported on the expandable stabilizer block, the position sensor to sensing a position of the at least one radially extendable cutter block relative to the tool body; and a vibration sensor to measure vibration of the tool, and the position sensor and the vibration sensor being in communication with a microprocessor to optimize drilling dynamics by comparing data.

18. A method of operating an expandable apparatus in a well to enlarge a borehole to a target dimension below a restriction, comprising:

locating a tool body in the borehole on a support below the restriction;

providing at least one cutter block radially movable from the retracted position substantially within the tool body to an expanded positioning radially outward of the tool body;

extending the at least one cutter block to an expansion diameter greater than the restriction;

rotating the apparatus while moving the apparatus axially along the borehole on the support while;

sensing a position of the at least one cutter block; and measuring vibration with a vibration sensor; and measuring wellbore diameter with a calliper element;

wherein block positional data is compared with data from the vibration sensor and data from the calliper element to optimize drilling.

19. The method of claim 18, further comprising:

recording the position of the at least one cutter block.

20. The method of claim 18, further comprising:

forwarding data using at least one mud pulse to a surface interface wherein the surface interface controls movement of the drill sting.

21. The method of claim 18, wherein the position sensor includes a strip and a sensor, one of the strip and the sensor supported on the cutter blade and the other of the strip and the sensor supported on the tool body.

* * * * *